United States Patent
Smith (12)

(10) Patent No.: US 6,468,805 B1
(45) Date of Patent: *Oct. 22, 2002

(54) AUTOMATED ANALYZER TESTING OF URINE FOR PRESENCE OF A PH ABNORMALITY

(75) Inventor: Jack V. Smith, St. Petersburg, FL (US)

(73) Assignee: Chimera Research and Chemical Inc., Deerfield, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/431,889

(22) Filed: May 1, 1995

Related U.S. Application Data

(60) Continuation-in-part of application No. 08/181,868, filed on Jan. 13, 1994, now abandoned, which is a continuation of application No. 07/848,245, filed on Mar. 9, 1992, now abandoned, which is a division of application No. 07/599,856, filed on Oct. 10, 1990, now abandoned.

(51) Int. Cl.$^7$ ................................................. G01N 31/16
(52) U.S. Cl. .................... 436/163; 435/7.9; 435/7.72; 436/166; 436/63; 436/504; 422/82.05
(58) Field of Search ................................ 436/163, 166, 436/901, 63, 504; 252/408.1; 424/7.1; 435/7.72, 7.9; 422/82.05, 82.09

(56) References Cited

U.S. PATENT DOCUMENTS

| | | | |
|---|---|---|---|
| 3,122,420 A | | 2/1964 | Rebar et al. |
| 3,146,070 A | * | 8/1964 | Collins ........................ 436/163 |
| 4,769,215 A | * | 9/1988 | Ehrenkranz ................. 432/102 |
| 4,806,487 A | | 2/1989 | Akers et al. |
| 4,822,743 A | | 4/1989 | Wegrzyn |
| 4,960,585 A | | 10/1990 | Tehrani |
| 5,049,358 A | | 9/1991 | Lau |
| 5,069,878 A | * | 12/1991 | Ehrenkranz ................... 422/61 |
| 5,077,222 A | * | 12/1991 | Lau .............................. 436/88 |
| 5,096,813 A | | 3/1992 | Krumhar et al. |
| 5,464,775 A | * | 11/1995 | Smith .......................... 436/63 |

FOREIGN PATENT DOCUMENTS

| | | | |
|---|---|---|---|
| JP | 58007946 | | 2/1974 |
| JP | 58007946 | * | 2/1983 |

OTHER PUBLICATIONS

CRC Handbook of Chemistry and Physics 63$^{rd}$ edition 1982–1983.*

Weast; 1982–83; CRC Handbook of Chemistry and Physics pp. D–157 to D–158.

Ames; Dec. 1992; Package Insert for Ames Reagent Strips.

* cited by examiner

*Primary Examiner*—Sheela Huff
(74) *Attorney, Agent, or Firm*—Herbert W. Larson

(57) ABSTRACT

In an automated analyzer containing a spectrophotometer for determining color changes in a urine sample the urine is admixed with a basic indicator effecting the first color change and an acidic indicator effecting a second color change, a surfactant and water. The spectrophotometer determines and prints whether a first or second color change has occurred.

5 Claims, No Drawings

AUTOMATED ANALYZER TESTING OF URINE FOR PRESENCE OF A PH ABNORMALITY

This application is a continuation-in-part of application Ser. No. 08/181,868, filed Jan. 13, 1994, now abandoned, which is a continuation of Ser. No. 07/848,245, filed Mar. 9, 1992, now abandoned, which is a divisional of application Ser. No. 07/599,856, filed Oct. 10, 1990, now abandoned.

This invention relates to a single reagent for use in determining pH in urine, or other fluids, being screened for drugs of abuse. This invention is particularly useful in automated analyzers used in screening for drugs of abuse.

As the use of illicit drugs in the workplace, public transportation, professional and amateur athletics and the like has grown, public concern for the health and safety of individuals, as well as concern for the negative impact of such drug use on productivity of industry, and its inherent economic impact, and the general well being and health of the community at large has grown as well. Such concern has led to the use of analysis of urine as a way to detect and deter drug use. Such testing for drugs of abuse in industry, as for prospective and current employees, military personnel, transportation employees, professional and amateur athletes, as well as people under supervision of the criminal justice system, has become a relative common occurrence.

Because of the intrusive nature of such testing commonly performed by examining a urine sample, the testing procedure must withstand vigorous scrutiny. Since a positive test result of screening for drugs of abuse may have serious impact on the life of a person being tested, the incentive for the drug user to alter the test specimen is high. The users of drugs of abuse have developed a number of ways to adulterate the collected specimen, thus attempting to produce a false negative result in the drug screening test being conducted.

A user of drugs of abuse may attempt to affect the test results, thus producing a false negative test result, or upon occasion, a false positive result, as by: 1) dilution—efforts to reduce the drug concentration in the urine sample; b) substitution for liquids such as clean (that is, drug-free) urine, soda, tea, apple juice for the drug-containing sample; or c) adulteration—addition to the urine specimen of foreign material in an attempt to invalidate the test.

Illicit drug users have learned to falsify urine screening tests by in vitro adulteration of urine sample by the addition of several readily available agents, including household products, among others, NaCl, soap, such as hand or dish soap, bleach, vinegar, Drano, $NaHCO_3$, Visine, Gold Seal Tea (available in natural food stores), or ($H_2 O_2$).

Additionally, users of drugs of abuse may eliminate some drugs more rapidly from their bodies by altering their urinary pH. Abusers of phencyclidine or amphetamines may be treated with $NH_4Cl$ to hasten detoxification, thus increasing the rate at which substances (phencyclidine or amphetamines) are eliminated from their bodies. This treatment with $NH_4Cl$ also results in lowering the pH of the user's urine.

While the use of some in vitro adulterants can be eliminated by the direct observation of the test subject during the collection process, such direct observation is often deemed unacceptable. In vivo adulterants represent an additional burden to the screening processor because they are consumed by the drug user several hours or days prior to screening of the sample, and can be detected only by laboratory means.

Such adulteration can affect all three commonly used methods for drugs of abuse, namely: florescent polarization immunoassay (FPIA), radioimmunoassay (RIA), and enzyme immunoassay (EMIT or EIA). Consequently, clinical chemistry literature recommends that testing for drugs of abuse in urine samples include testing for adulterants to identify urine samples which have been adulterated. See Mikkelsen and Ash, "Adulterants Causing False Negatives In Illicit Drug Testing", Clin. Chem. 34/11, 2333–2336 (1988); and Warner, "Interference of Common Household Chemicals In Immunoassay Methods For Drugs Of Abuse", Clin. Chem., 35/4, 648–651 (1989).

Accordingly, a need exists for providing an easy and convenient manner by which to make a determination of the presence of adulterants in urine samples which are being tested for drugs of abuse. A further need exists for a convenient manner by which such determinations may be made in conjunction with an automatic analyzing process for drugs of abuse.

SUMMARY OF THE INVENTION

The present invention relates to a single reagent to detect simultaneously multiple levels of pH in urine or other fluids. This reagent is designed to be used on automated analyzers used for drugs of abuse testing.

The purpose of the reagent is to facilitate the conducting of pH testing simultaneously while conducting drug tests on the same automatic analyzer. Specifically, if the pH of the urine, or other sample fluid being tested, is out of the normal range, that is, greater than 9.0 or less than 4.5, such variation from the normal range will cause false negative readings, or in some cases false positive readings when tested by three of the above-noted most common drug-screening methods; namely, EIA (enzyme immunoassay), FPIA (fluorescent polarization immunoassay), and RIA (radio-immunoassay.)

Use of the reagent of this invention permits the technician conducting the test to halt the testing process, or assay, as soon as the out-of-range pH determination is made. The ability to terminate the screening process by ascertaining that the pH is out of range, and therefore presumably adulterated, would result in reduced technician's efforts and time, providing an economic savings to the testing laboratory. Furthermore, the early interruption and cessation of the automated screening process may facilitate earlier obtention of a substitute specimen from the person being tested, providing more accurate determinations to the agency which had determined the original necessity for the test.

The use of the instant reagent permits the determination of pH of the testing sample to be done by the automated substance abuse testing program, rather than the relatively cumbersome methods of pH test (litmus) paper, which must be dipped in the urine, or by pH metering.

The instant reagent comprises an aqueous solution of two different pH indicators that effect a color change, specifically one indicator for basic, or high pH, and one for acidic, or low pH, wherein further, the solution contains a surfactant and is adjusted to a predetermined pH point.

DETAILED DESCRIPTION OF THE INVENTION

The pH reagent of the instant invention comprises an aqueous solution of a basic indicator which effects a color change, an acidic indicator which effects a color change, a surfactant and NaOH or HCl solution to adjust to a pH of 6.0.

Suitable basic indicators for use in the instant invention comprise bromcresol green, bromphenol blue, tetrabromphenol blue or brom-chlorphenol blue.

Suitable acidic indicators comprise thymol blue, bromothymol blue, metacresol purple or phenolphthalein.

The preferred surfactant is a brij 35 solution of polyoxyethylene 23 lauryl ether, 30% by weight in the total solution volume.

Upon completion of the preparation of the reagent, the reagent solution is adjusted to pH 6.0, using NaOH or HCl, as appropriate. At pH of 6.0, the solution is green in color.

The following is an illustration of the preparation of the pH reagent according to the invention.

EXAMPLE I

| | | |
|---|---|---|
| 0.01 g | bromcresol green | |
| 0.01 g | thymol blue | |
| 0.5 ml | brij 35 solution, 30% weight/volume (polyoxyethylene 23 lauryl ether) | | pH of the solution is adjusted to 6.0 with NaOH or HCl; quantity sufficient total volume to 1.0 liter with reagent grade distilled water for working solution.

The formulation is prepared by measuring the quantities of, bromothymol blue sodium salt, bromcresol green and thymol blue into a 1-liter flask; 750 ml reagent-grade distilled water is added to the flask, with mixing of the formulation begun; 0.5 ml brij 35 solution is pippetted into the flask; the solution is mixed for 30 minutes, at which time the pH of the reagent solution is adjusted to 6.0 with NaOH or HCl. Sufficient quantity of reagent grade distilled water is added to bring the total volume of the solution in the flask to 1.0 liter.

In the Example immediately above, in lieu of the stated bromcresol green, one may substitute 0.01 g bromphenol blue, tetrabromphenol blue or brom-chlorphenol blue. In lieu of the thymol blue in the Example above, one may substitute 0.01 g bromothymol blue, metacresol purple or phenolphthalein. The substituted formulations are prepared in the same manner as that listed in the Example above.

The reagent of the instant invention is intended for mixing with urine samples and placement in a cuvette of an automatic analyzer, such as enzyme immunoassay analyzers (EMIT), such as Olympus AU 5000 series, Monarch, Hitachi 700 series, among others. On these instruments, the reagent is used in a 30 to 1 ratio of reagent to urine sample (i.e. 300 L reagent to 10 L sample). The instrument spectrophotometer is set at 600 nm, and the acceptable pH range is set by running 3.5 11.4, 9.0 buffers, at the beginning of the run to use the values of the buffers to establish ranges for the run.

In the instant invention, when urine which has been adulterated to acidic pH ranges is mixed in the prescribed ratio with the instant reagent, the color of the solution turns from green to a light, yellow color. Similarly, when the reagent of the instant invention is mixed in the prescribed ratio with urine which has been adulterated to basic pH ranges, the solution turns from green to a dark, blue color. Such indication may be seen in a manual inspection, but is especially intended for use in automatic analysis, such as those which employ spectrophotometric means of inspection.

Specifications for running the urine samples through three specific instruments, of the enzyme immunoassay type (EMIT) Olympus, Hitachi and Monarch, are listed below. The settings are intended as guidelines, and are set forth with the understanding that those skilled in the art would recognize that such parameters will vary slightly from instrument to instrument, (as from Hitachi 705/Hitachi 717). The suggested specifications are as follows:

| SETTINGS: | OLYMPUS | HITACHI | MONARCH |
|---|---|---|---|
| Measuring point | S-0 | range 1–14 | data points: 1 |
| | E-# | K factor 0 | Algorith: lin |
| Reagent O.D. | −2.00 to 2.00 | −2.00 to 2.00 | −2.00 to 2.00 |
| Normal H | 1000 | sen: max | Interval: 30 sec |
| sample vol. | 10 l | 10 l | 8 l |
| Reagent vol. | 300 l | 300 l | 220 l |
| wave: | 600 nm | 600 nm | 600 nm |
| slope | + | abs: + | optical: abs |
| calibration method | m-cal | S.D. limit 999 | Rgt. Blk.: off |
| factor: | 10,000 | Dup. lim.: 30,000 | Ref. Type: dil. |
| concentration | 0 | Inst. factor: 1 | Delay: 30 sec. |

Set forth immediately below are the results of a test of a series of urine samples which included adulterated urine. The samples were mixed with the reagent of the instant invention, in the prescribed ratio of 30:1, and tested for pH on a Hitachi 717 instrument. The reagent used was the formulation comprising: 0.01 g each of bromcresol green, bromothymol blue sodium salt, and thymol blue, 0.5 ml brij 35 solution, with pH adjusted to 6.0 and the solution brought to 1.0 liter with reagent grade distilled water.

Further, the pH of each of the samples was checked by means of a pH meter. The comparison is set forth below:

| SAMPLE NO. | ADULTERATED/ NON-ADULTERATED | AUTOMATED pH READING | pH METER |
|---|---|---|---|
| C118 | A | 3.5 | 4.0 |
| C218 | A | 3.5 | 4.0 |
| C318 | NA | 7.0 | 7.0 |
| C418 | NA | 6.9 | 7.0 |
| E082-001 | A | 3.5 | 4.0 |
| E083-002 | A | 4.6 | 4.5 |
| E084-003 | NA | 6.7 | 7.0 |
| E085-004 | NA | 6.9 | 7.0 |
| E086-005 | INCONCLUSIVE | 8.8 | 8.9 |
| E087-006 | A | 10.7 | 10.0 |
| E088-007 | A | 11.4 | 11.0 |
| C119 | A | 3.5 | 4.0 |
| C219 | A | 3.5 | 4.0 |
| C319 | A | 4.9 | 5.0 |

Another example of the pH reagent of the instant invention comprises an aqueous solution of a basic indicator which effects a color change, an acidic indicator which effects a color change and a third indicator which is acidic, basic, or neutral and in combination with the first two indicators yields an enhanced linear response.

Suitable basic indicators for use in the instant invention comprise bromcresol green, bromphenol blue, tetrabromphenol blue or brom-chlorphenol blue.

Suitable third indicators comprise bromthymol blue sodium salt, quindine blue, neutral red, or rosolic acid aurin.

Suitable acidic indicators comprise thymol blue, bromothymol blue, metacresol purple or phenolphthalein.

The preferred surfactant is a brij 35 solution of polyoxyethylene 23 lauryl ether, 30% by weight in the total solution volume.

Upon completion of the preparation of the reagent, the reagent solution is adjusted to pH 6.0, using NaOH or HCl, as appropriate. At pH of 6.0, the solution is green in color.

The following is an illustration of the preparation of the pH reagent according to the invention using three indicators.

EXAMPLE II

| | |
|---|---|
| 0.01 g | bromothymol blue sodium salt |
| 0.01 g | bromcresol green |
| 0.01 g | thymol blue |
| 0.5 ml | brij 35 solution, 30% weight/volume (polyoxyethylene 23 lauryl ether) | pH of the solution is adjusted to 6.0 with NaOH or HCl; quantity sufficient total volume to 1.0 liter with reagent grade distilled water for working solution.

The formulation is prepared by measuring the quantities of bromcresol green and thymol blue into a 1-liter flask; 750 ml reagent-grade distilled water is added to the flask, with mixing of the formulation begun; 0.5 ml brij 35 solution is pippetted into the flask; the solution is mixed for 30 minutes, at which time the pH of the reagent solution is adjusted to 6.0 with NaOH or HCl. Sufficient quantity of reagent grade distilled water is added to bring the total volume of the solution in the flask to 1.0 liter.

In the example immediately above, in lieu of the stated bromcresol green, one may substitute 0.01 g bromphenol blue, tetrabromphenol blue or brom-chlorphenol blue. In lieu of the thymol blue in the Example Formulation, one may substitute 0.01 g bromothymol blue, metacresol purple or phenolphthalein. In lieu of the bromothymol blue sodium salt in the Example Formulation, one may substitute 0.01 g quidine blue, neutral red, or resolic acid aurin. The substituted formulations are prepared in the same manner as that listed in the Example above.

The reagent of the instant invention is intended for mixing with urine samples and placement in a cuvette of an automatic analyzer, such as enzyme immunoassay analyzers (EMIT), such as Olympus AU 5000 series, Monarch, Hitachi 700 series, among others. On these instruments, the reagent is used in a 30 to 1 ratio of reagent to urine sample (i.e. 300 L reagent to 10 1 sample). The instrument spectrophotometer is set at 600 nm, and the acceptable pH range is set by running 3.5 11.4, 9.0 buffers, at the beginning of the run to use the values of the buffers to establish ranges for the run.

In the instant invention, when urine which has been adulterated to acidic pH ranges is mixed in the prescribed ratio with the instant reagent, the color of the solution turns from green to a light, yellow color. Similarly, when the reagent of the instant invention is mixed in the prescribed ratio with urine which has been adulterated to basic pH ranges, the solution turns from green to a dark, blue color. Such indication may be seen in a manual inspection, but is especially intended for use in automatic analysis, such as those which employ spectrophotometric means of inspection.

Specifications for running the urine samples through three specific instruments, of the enzyme immunoassay type (EMIT) Olympus, Hitachi and Monarch, are listed below. The settings are intended as guidelines, and are set forth with the understanding that those skilled in the art would recognize that such parameters will vary slightly from instrument to instrument, (as from Hitachi 705/Hitachi 717). The suggested specifications are as follows:

| SETTINGS: | OLYMPUS | HITACHI | MONARCH |
|---|---|---|---|
| Measuring point | S-0 | range 1–14 | data points: 1 |
| | E-# | K factor 0 | Algorith: lin |
| Reagent O.D. | −2.00 to 2.00 | −2.00 to 2.00 | −2.00 to 2.00 |
| Normal H | 1000 | sen: max | Interval: 30 sec |
| sample vol. | 10 1 | 10 1 | 8 1 |
| Reagent vol. | 300 1 | 300 1 | 220 1 |
| wave: | 600 nm | 600 nm | 600 nm |
| slope | + | abs: + | optical: abs |
| calibration method | m-cal | S.D. limit 999 | Rgt. Blk.: off |
| factor: | 10,000 | Dup. lim.: 30,000 | Ref. Type: dil. |
| concentration | 0 | Inst. factor: 1 | Delay: 30 sec. |

The reagent of the instant invention may also be used on instruments which use fluorescent polarization immunoassay techniques (FPIA) and radioimmunoassay (RIA) technology without departing from the scope of the invention.

It will be understood that the embodiments described herein are merely exemplary and that a person skilled in the art may make variations and modifications without departing from the spirit and scope of the invention. All such modifications and variations are to be included within the scope of the invention as defined in the appended claims.

What is claimed is:

1. A process for testing urine for normal or adulterated condition by determining the pH of the urine in an automated analyzer comprising the steps of admixing a urine sample with a reagent solution having as components thereof a basic indicator which effects a first color change and an acidic indicator which effects a second color change, a surfactant and water with pH adjusted to about. 6.0, placing the mixed urine/reagent sample in a cuvette within the automated analyzer, and comparing colors by spectrophotometry means within the automated analyzer to determine whether a first or a second color change has occurred and thereby confirm the presence or absence of an adulterant while simultaneously conducting a test for drugs present in the urine sample.

2. The process of claim 1 wherein the determination of urine pH is measured within the range of 3.5 to 11.4 pH units.

3. The process of claim 1 wherein the admixing of urine sample to reagent is at a ratio of 1 to 30 by volume.

4. The process of claim 1 wherein the spectrophotometer is set at about 600 nm when determining the first or second color change.

5. The process of claim 1 wherein the reagent components are bromcresol green, thymol blue, a surfactant, water and sufficient sodium hydroxide or hydrogen chloride to adjust the reagent solution to a pH about 6.0.

\* \* \* \* \*